United States Patent [19]
Ling et al.

[11] Patent Number: 5,470,336
[45] Date of Patent: Nov. 28, 1995

[54] SYSTEM FOR PERFORMING HIP PROSTHESIS REVISION SURGERY

[76] Inventors: Robin S. M. Ling, 2 The Quadrant, Wonford Road, Exeter, EX2 4LE, England; W. E. Michael Mikhail, 4203 Shamley Green, Toledo, Ohio 43623; James J. Elting, Otsego Orthopaedics, One Associate Dr., Oneonta, N.Y. 13820; Graham A. Gie, 2 The Quadrant, Wonford Road, Exeter, EX2 4LE, England; Tom J. J. H. Slooff, c/o University Hospital, St. Radboud, Th. Craanenlaan 7, Postbus 9101, 6500 HB Nijmegen, Netherlands; Jacques J. Vanderlinden, 4 Avenue d'Evian, 1006 Lausanne, Switzerland

[21] Appl. No.: 143,272

[22] Filed: Oct. 26, 1993

Related U.S. Application Data

[60] Continuation of Ser. No. 939,054, Sep. 2, 1992, abandoned, which is a division of Ser. No. 735,524, Jul. 23, 1991, Pat. No. 5,192,283, which is a continuation-in-part of Ser. No. 565,149, Aug. 10, 1990, Pat. No. 5,047,035.

[51] Int. Cl.⁶ ..................................................... A61F 2/28
[52] U.S. Cl. ................................ 606/105; 606/92; 606/95; 606/96; 606/99; 623/16; 623/18
[58] Field of Search .................................. 623/16, 18, 23; 606/92, 93, 94, 95, 96, 99, 105

[56] References Cited

U.S. PATENT DOCUMENTS

| | | |
|---|---|---|
| 4,686,972 | 8/1987 | Kurland . |
| 4,815,454 | 3/1989 | Dozier et al. . |
| 4,846,161 | 7/1989 | Roger . |
| 4,860,735 | 8/1989 | Davey et al. . |
| 4,865,608 | 9/1989 | Brooker, Jr. ........................ 623/18 |
| 4,873,969 | 10/1989 | Huebsch . |
| 4,896,662 | 1/1990 | Noble . |
| 4,919,153 | 4/1990 | Chin . |
| 4,919,673 | 4/1990 | Willert et al. . |
| 4,919,679 | 4/1990 | Averill et al. . |
| 4,963,155 | 10/1990 | Lazzeri et al. . |
| 4,986,826 | 1/1991 | Roger . |
| 4,994,085 | 2/1991 | Sawai et al. . |
| 5,021,063 | 6/1991 | Tager . |
| 5,047,035 | 9/1991 | Mikhail et al. . |
| 5,061,287 | 10/1991 | Feiler . |
| 5,078,746 | 1/1992 | Garner . |
| 5,108,405 | 4/1992 | Mikhail et al. ..................... 606/96 |
| 5,192,283 | 3/1993 | Ling et al. ......................... 606/92 |

FOREIGN PATENT DOCUMENTS 2615097  11/1988  France .

OTHER PUBLICATIONS

Insall, "Principles and Techniques of Knee Replacement" 1983, pp. 20–21.
Insall/Burstein, "Total Knee System", 1981—Brochure by Zimmer, Inc.
"Economy is the mother of a cement removal technique", Sep., 1989, issue of *Orthopaedics Today*, pp. 18 & 19.

*Primary Examiner*—Paul B. Prebilic
*Attorney, Agent, or Firm*—Emch, Schaffer, Schaub & Porcello Co.

[57] ABSTRACT

An apparatus for performing hip prosthesis revision surgery includes means for preparation of the cavity left after removal of the original prosthesis. A tamp having a longitudinal passageway extending longitudinally through the stem portion thereof and a guidewire positioned in the cavity function to compact bone graft material in the cavity and form a precisely contoured new hip prosthesis receiving cavity.

3 Claims, 8 Drawing Sheets

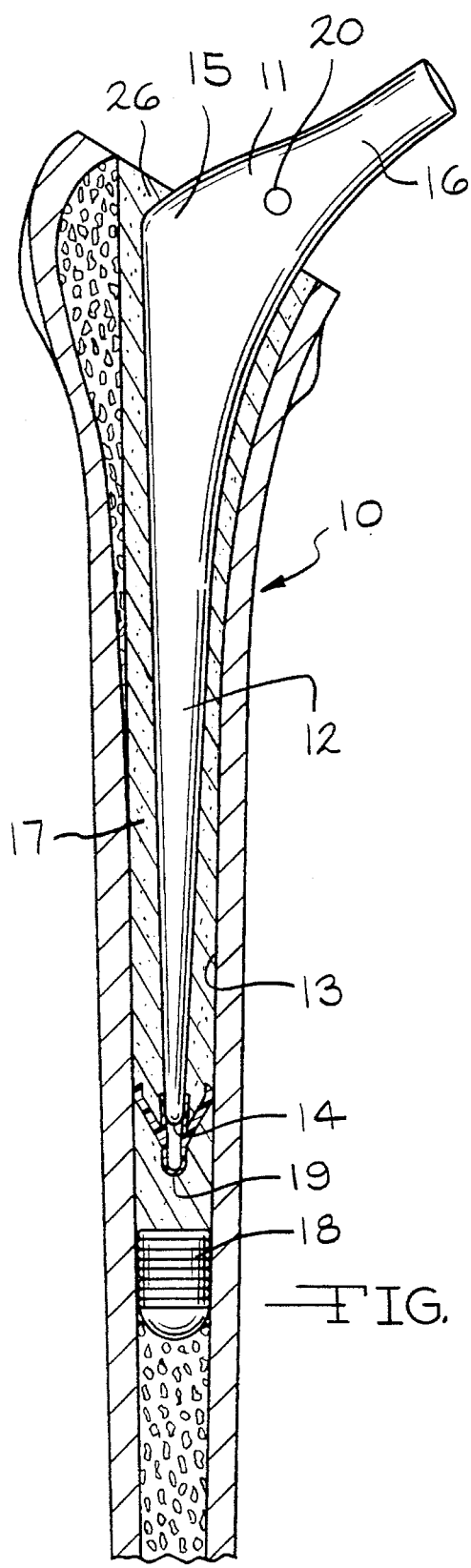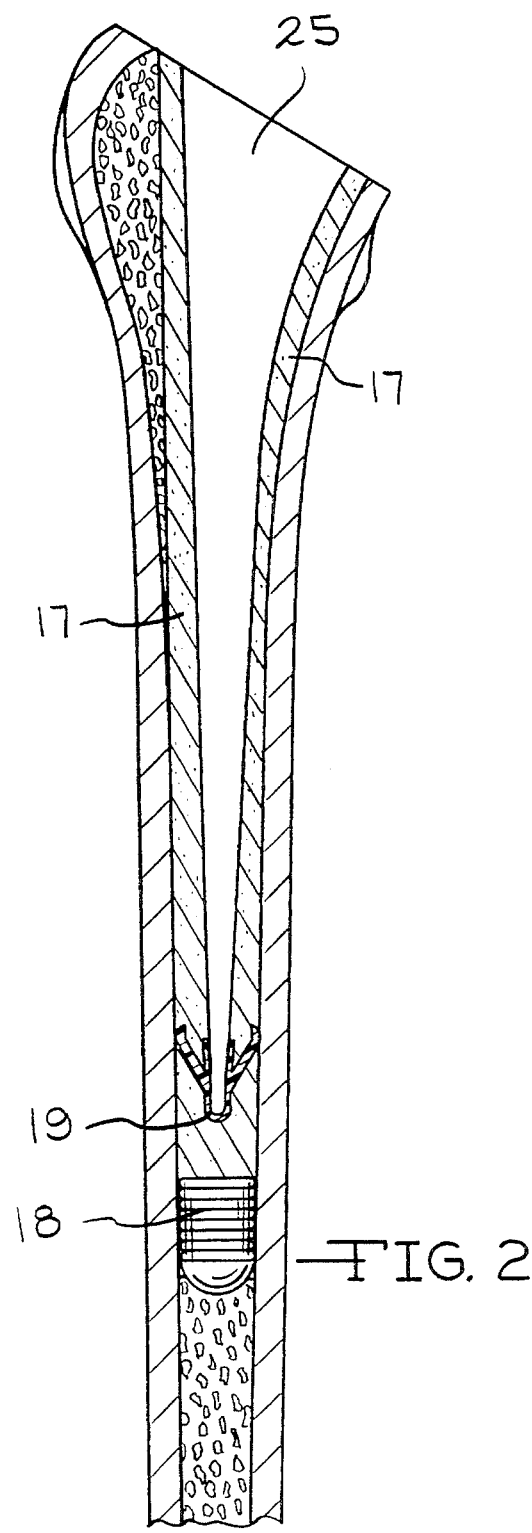

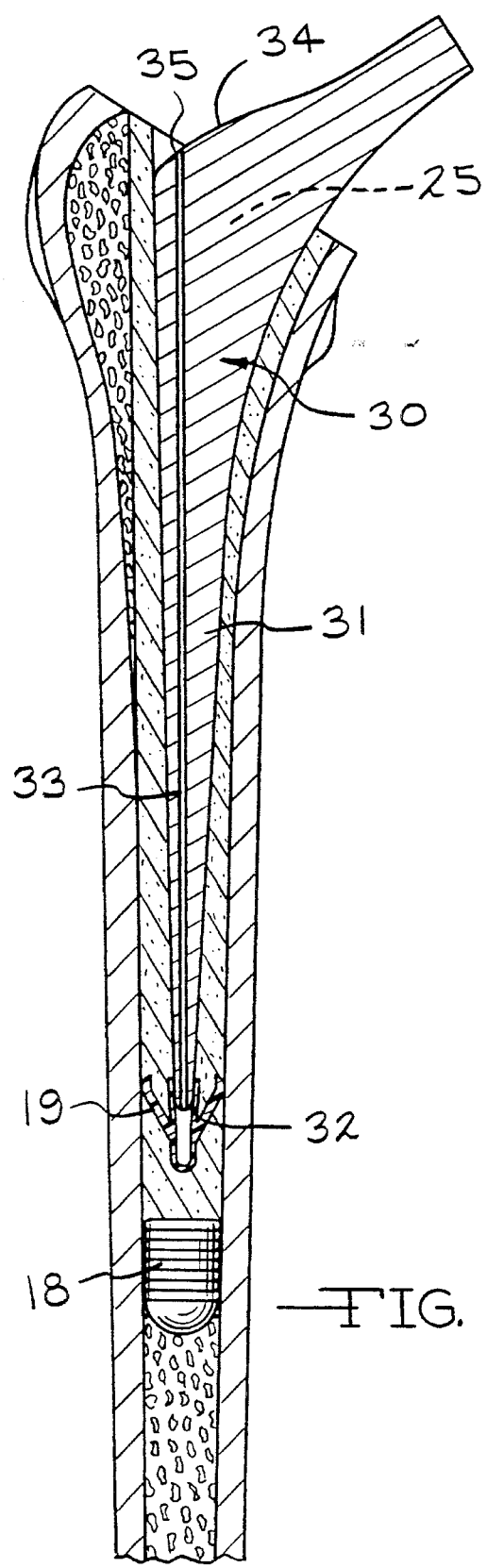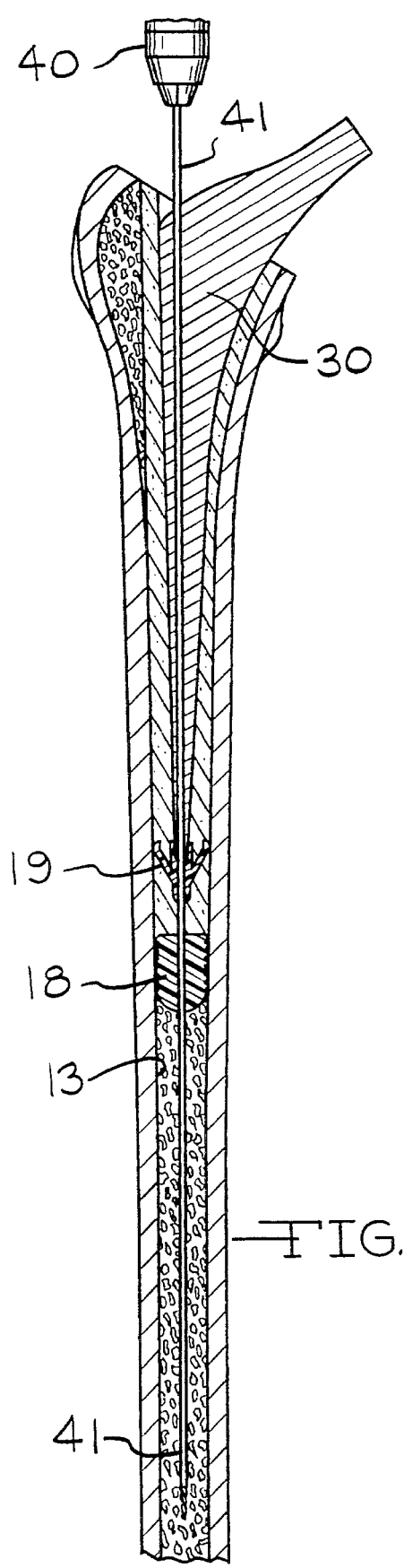

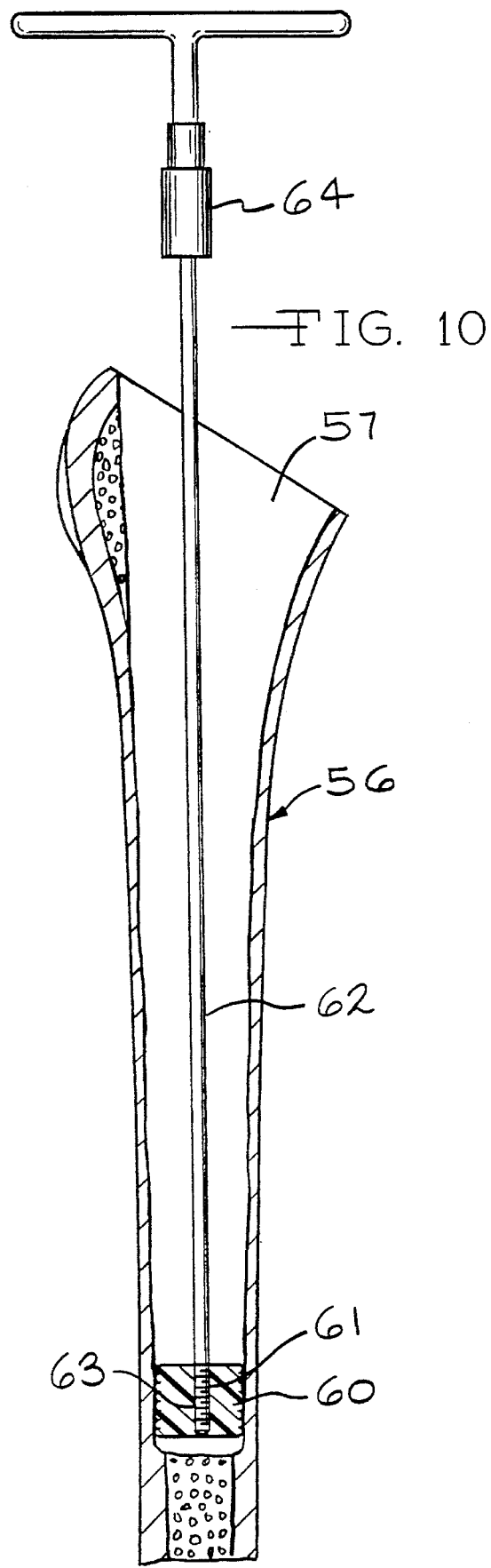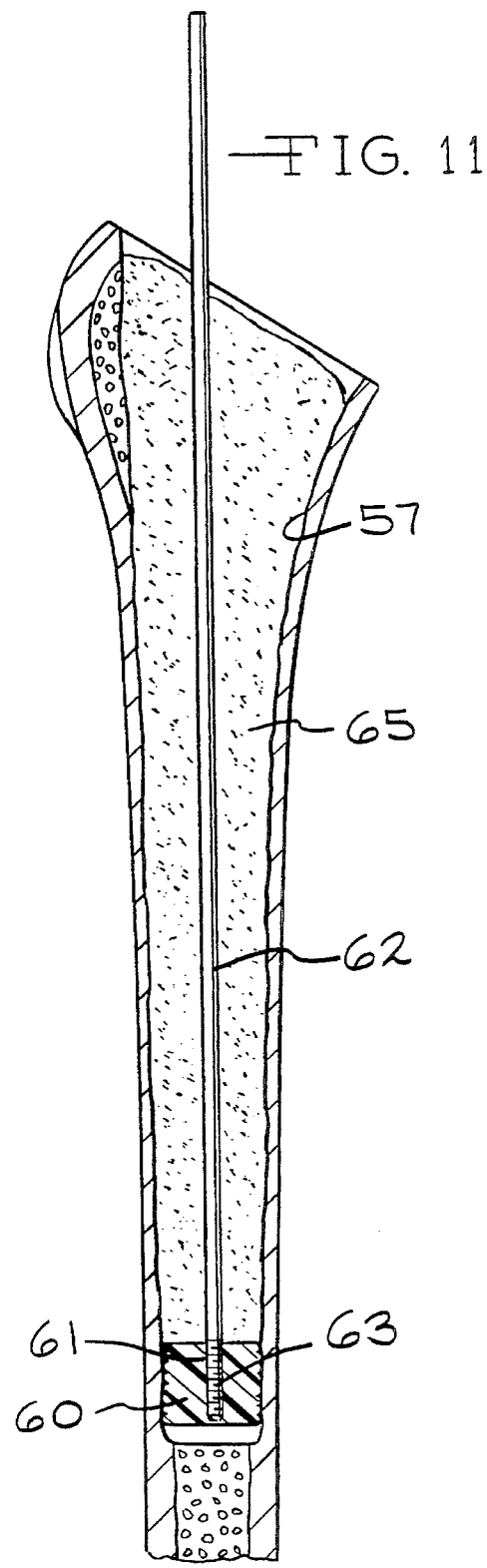

SYSTEM FOR PERFORMING HIP PROSTHESIS REVISION SURGERY

CROSS REFERENCE TO RELATED APPLICATION

This is a continuation of U.S. application Ser. No. 07/939,054 filed Sep. 2, 1992 (abandoned) which is a division of U.S. application Ser. No. 07/735,524 filed Jul. 23, 1991, now U.S. Pat. No. 5,192,283, which is a continuation-in-part of U.S. application Ser. No. 07/565,149, filed Aug. 10, 1990, now U.S. Pat. No. 5,047,035.

BACKGROUND ART

The present invention is directed to a method for performing revision surgery to replace a hip prosthesis having a stem portion previously implanted in the intramedullary canal of a femur and to a system for performing such surgery.

As is well known, it is frequently necessary to replace a hip joint prosthesis. This is usually done several years after the original implantation in order to replace dysfunctional joints or to obtain the benefits of one of newer design which resulted from advancements in medical technology.

In the course of hip revision surgery, it is necessary to remove the femoral component including its stem from the intramedullary canal of the femur. If cement material was used to fix the stem within the intramedullary canal, it must be removed prior to implantation of the new prosthesis therein. Removal of the cement is accomplished by drilling or reaming. During such drilling or reaming procedure, it is important that the drill or reamer be properly aligned and guided to avoid accidental perforation of the cortex of the femur.

A number of prior art devices have been utilized for aligning drills or reamers in the performance of revision hip surgery. U.S. Pat. No. 4,860,735 relates to a drill alignment guide for osteoplastic surgery in which an alignment rod is supported on a clamp element affixed to the femur. The drill is mounted for movement with an alignment rod which is parallel to and disposed a predetermined distance from a shaft of the drill. As the drill is moved forward, the forward end of the alignment rod moves through an aperture of the clamp element thereby insuring that drilling occurs along a predetermined drilled path extending along the bone axis.

U.S. Pat. No. 4,686,972 relates to a surgical deflector and drilling guide for guiding a drill bit, awl or reamer into a bone. The boring-tool guide assembly comprises a sleeve having a T-shaped nib which can be detachably inserted into a corresponding bracket permanently mounted against a tool having teeth designed to anchor the tool on a boney tissue. The surgeon can insert the tip of a drill bit, awl or reamer into the sleeve of the guide assembly when the teeth are anchored onto the boney tissue to obtain means for guiding the boring tool.

A method of economically removing cement from the femoral canal during revision surgery appeared in the publication "Orthopedics Today", Sep. 1989, pages 18 and 19. Under the procedure described therein, a side cut and end cut reamer positioned in a guide sleeve is utilized to remove the cement.

A catalog entitled "Omniflex™ Femoral System Surgical Protocol Press-Fit" copyright 1988 by Osteonics Corp., describes a cement removal system utilizing a tapered axial reamer.

U.S. Pat. No. 4,919,673 is directed to a femoral head prosthesis having a fixing stem, with a longitudinal bore utilizing a centering rod extending therethrough and engaged to a barrier at the lower end of the bone cavity.

Following removal of all of the old plastic cement and any cement restricter or plug which may have been used, the cavity remaining in the femur will be substantially larger than is necessary or desirable to accommodate the new femoral hip prosthesis. Accordingly, it is generally accepted procedure to place crushed cancellous bone graft in the enlarged cavity or femoral canal. Prior to positioning the new prosthesis in the femoral canal, the crushed cancellous bone graft is tamped in order to compact it and have it tightly packed in the femoral canal. The stem of the new prosthesis is then placed in the femoral canal with bone cement if the prosthesis is of the type intended for use with bone cement or without bone cement if such prosthesis is of a type intended to be used without such bone cement. If the crushed cancellous bone graft is tightly compacted prior to insertion of the stem of the new prosthesis therein, it may be necessary to enlarge the new cavity in the compacted crushed cancellous bone graft to receive the new prosthesis or use a smaller prosthesis than was intended. As is well known by those skilled in the art, it is necessary that the crushed cancellous bone graft be tightly compacted to provide for strong boney structure around the prosthesis and, if it is not compacted sufficiently tightly prior to introduction of the prosthesis, attempts must be made to further compact it after placement of the new prosthesis in the femoral canal.

The foregoing prior art references are incorporated herein by reference.

DISCLOSURE OF INVENTION

Application Ser. No. 07/565,149, filed Aug. 10, 1990, now U.S. Pat. No. 5,047,035 provides for a new method of performing revision surgery utilizing improved means for insuring proper centering and guidance of the reamer utilized for removing old bone cement. Such centering and guidance means insures proper positioning of the revision prosthesis with an adequate thickness of bone cement there around and assists in avoiding accidental perforation of the cortex of the femur. Under such invention, the original femoral component is removed and then replaced by a cannulated trial femoral component of similar size and shape to the original prosthesis which has been removed. X-rays taken prior to removal of the original prosthesis can be used to confirm that the original prosthesis is still properly aligned in the femoral canal and did not subside within the original cement mantle into varus. Assuming that the original prosthesis as removed was properly alighted, the cannulated trial femoral component is then inserted into the cavity left by the removal of the original prosthesis. an elongated drill is then inserted through the cannulated stem and, using the passageway of the cannulated stem as a guide, is utilized to drill through the cement and cement restricter at the bottom of the cavity thus forming a pilot hole in the cement, restricter and bone marrow therebelow. The pilot hole is sufficiently large to permit insertion of a bullit guidewire having a slightly enlarged head at its free end. Following insertion of the bullit guide wire, cannulated reamers of progressively increasing size are placed over the bullit guidewire and utilized to progressively increase the size of the prepared canal to (1) remove all of the old bone cement, centralizer and restricter and (2) reach a size suitable for receiving new bone cement and the stem of the new femoral hip joint prosthesis.

As previously discussed, removal of the old bone cement will result in formation of a cavity in the femur significantly larger than required or desired to receive the new prosthesis and a portion of such cavity should be filled with crushed cancellous bone graft which is then tightly compacted therein.

According to the present invention, a method is provided using a cannulated tamp of the present invention to compact crushed cancellous bone graft placed in such enlarged cavity to the density or tightness desired for optimum grafting with the remaining bone while at the same time forming a new cavity of the desired shape and size to receive the new prosthesis with the appropriate amount of bone cement. The present invention utilizing the cannulated tamp and guidewire may be used in revision surgery performed using alternate methods of removing bone cement as well as the method of removing bone cement disclosed in the parent U.S. application Ser. No. 07/565,149 filed Aug. 10, 1990, now U.S. Pat. No. 5,047,035.

Accordingly, it is object of the present invention to provide a method and apparatus for performing revision surgery including specifically a method and apparatus for placement and compacting of crushed cancellous bone graft in an enlarged cavity in a manner which forms a cavity of the shape and size desired to receive the stem of a hip prosthesis.

The invention will be more fully understood and other objects and advantages will become apparent from the following detailed description in conjunction with the attached drawings.

BRIEF DESCRIPTION OF THE DRAWINGS

FIG. 1 is an elevational view, partially in section, showing a femoral hip joint prosthesis implanted in the femoral canal of a patient.

FIG. 2 is a view similar to FIG. 1 showing the femur with the previously implanted femoral hip joint prosthesis removed.

FIG. 3 is a view similar to FIGS. 1 and 2 showing the cannulated trial femoral component of the present invention positioned within the cavity previously occupied by the original femoral hip joint prosthesis.

FIG. 4 is a view similar to FIG. 3 but showing the drilling of a pilot passageway utilizing the cannulated trial femoral component as a guide.

FIG. 10 is a sectional view of a femur prepared for revision surgery showing placement of a new cement restricter.

FIG. 11 is a view similar to FIG. 10 showing the next step of revision surgery.

BEST MODE OF CARRYING OUT INVENTION

Figure 5:
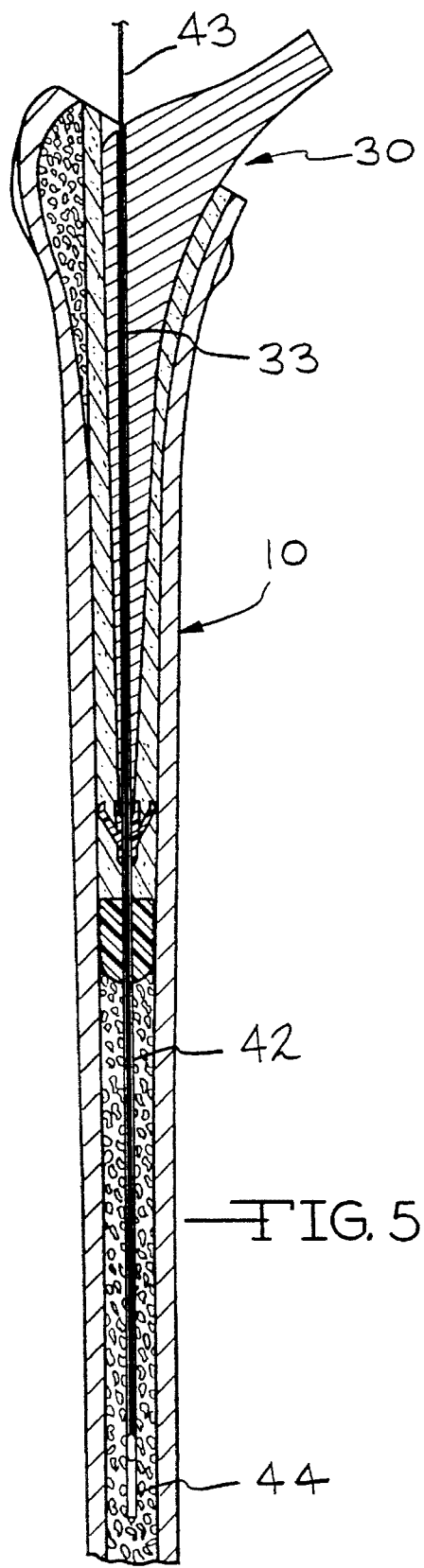
FIG. 5 is a view similar to FIG. 4 following removal of the elongated drill bit and insertion of the guidewire with its enlarged bullit head through the guide passageway of the cannulated trial femoral component and into the newly drilled pilot hole.

Referring new to FIG. 1, there is shown a femur generally designated by the number 10 having implanted therein a hip joint prosthesis 11 having a stem 12 implanted within the intramedullary canal 13 of the femur. The stem extends from a lower distal end 14 to an upper portion which includes an enlarged shoulder 15 and a neck portion 16 disposed at an obtuse angle relative to the stem 12.

The prosthesis 11 is typically secured in the femoral intramedullary canal 13 by a cement mantle 17 of polymethylmethacrylate (PMMA) or other suitable bone cement. A restricter 18 is placed in the intramedullary canal 13 prior to introduction of the bone cement 17 therein. The distal end 14 of the stem may be engaged in a centralizer 19 which assists in centering the distal end 14 during the step of implantation of the prosthesis 11 in the cement 17. The prosthesis 11 may be provided with an aperture 20 or other suitable grasping means to assist in its removal. As shown in FIG. 2, the removal of the prosthesis 11 leaves a cavity 25 conforming to the shape of the removed stem 12. Obviously, prior to removal of the prosthesis 11, any portion of the cement mantle 17 such as that overlying the enlarged shoulder 15 as indicated by the numeral 26 in FIG. 1, must be removed. As can be seen in FIG. 2, the restricter 18 and centralizer 19 remain within the intramedullary canal 13 following removal of the prosthesis 11 as does the cement mantle 17 which retained the prosthesis 11.

It is desirable that all of the old cement 17 be removed prior to implantation of a new prosthesis in the intramedullary canal 13. In order to effect such cement removal efficiently and with minimal risk to the patient, guide means for the drill and reamer are utilized for such removal. Referring to FIG. 3, there is shown a cannulated trial femoral component 30 following its insertion into the cavity 25 left by removal of the original prosthesis 11. The cannulated trial femoral component 30 preferably has a stem 31 which is shaped substantially the same as the shape of the stem of the original prosthesis 11. The stem 31 extends from a distal end 32 to an enlarged upper end 34 extending out of the cavity 25. The stem 31 has a longitudinally extending passageway 33 which extends from the distal end 32 to the upper end 34 where it forms an outlet opening 35.

Prior to removal of the original prosthesis 11, X-rays should be taken to determine that the stem 12 of such original prosthesis was properly aligned in the intramedullary canal 13 and that it did not shift into varus as a result of subsidence within the cement mantle. such subsidence within the cement mantle is known to occur over a period of time.

As shown in FIG. 4, there is provided a drill 40 having an elongated drill bit 41. The drill bit 41 has a length permitting it to extend completely through the longitudinal passageway 33 of the cannulated trial femoral component 30 and a substantial distance beyond. Thus, as shown in FIG. 4, the drill bit 41 is of sufficient length to drill, using the longitudinal passageway 33 as a guide, through the centralizer 19, restricter 18 and a substantial distance into the intramedullary canal 13 forming a new channel 42 below the restricter 18.

Referring now to FIG. 5, there is shown a bullit guidewire 43 having an enlarged head 44 positioned in the newly drilled channel 42.

Thus, following drilling of the channel 42 through the centralizer 19, restricter 18 and further into the intramedullary canal 13, the drill bit 41 is removed therefrom while leaving the cannulated trial femoral component 30 positioned therein. Thereafter, the guidewire 43 with its enlarged head 44 is inserted through the longitudinal passageway 33 and into the channel 42. Following insertion of the guidewire 43, the cannulated trial femoral component 30 is removed leaving the guidewire 43 in position.

Figure 6:
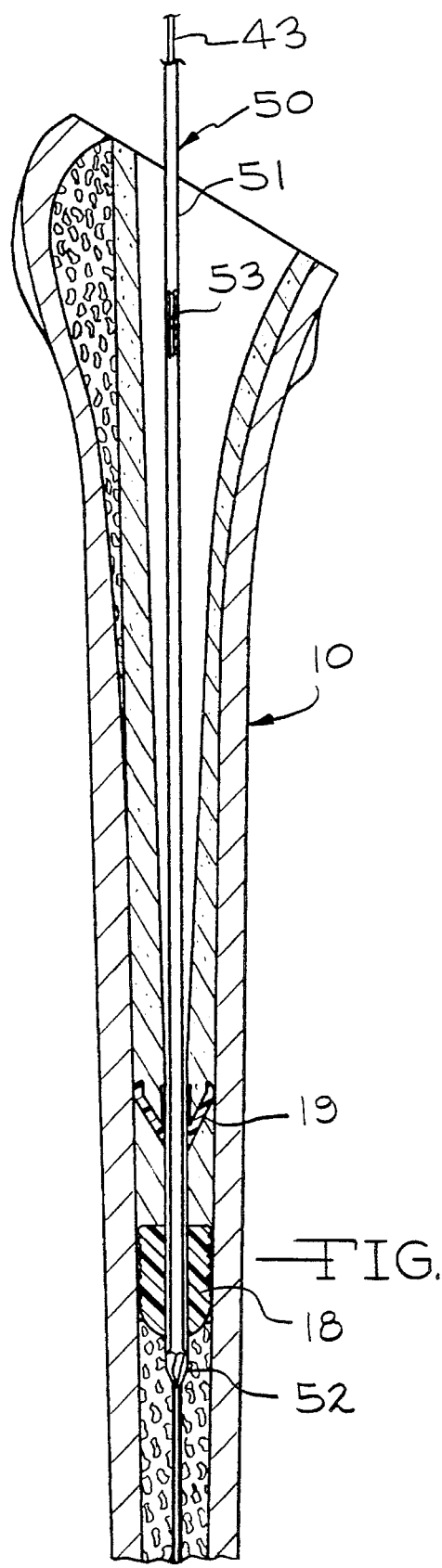
FIG. 6 is a view similar to FIG. 5 but slightly enlarged for clarity, showing the reaming of the canal following removal of the cannulated trial stem and showing the first of several progressively larger reamers being utilized with the bullit guidewire as a guide to control the path of the reamer.

Referring now to FIG. 6, following removal of the cannulated trial femoral component 30, a reamer 50 having a hollow stem 51 terminating in an enlarged cutting head 52 is provided. A longitudinal passageway 53 extends through the cutting head 52 and the stem 51. The reamer 50 is telescoped over the bullit guidewire 43 and may be power rotated by any standard well known power means.

Figure 7:
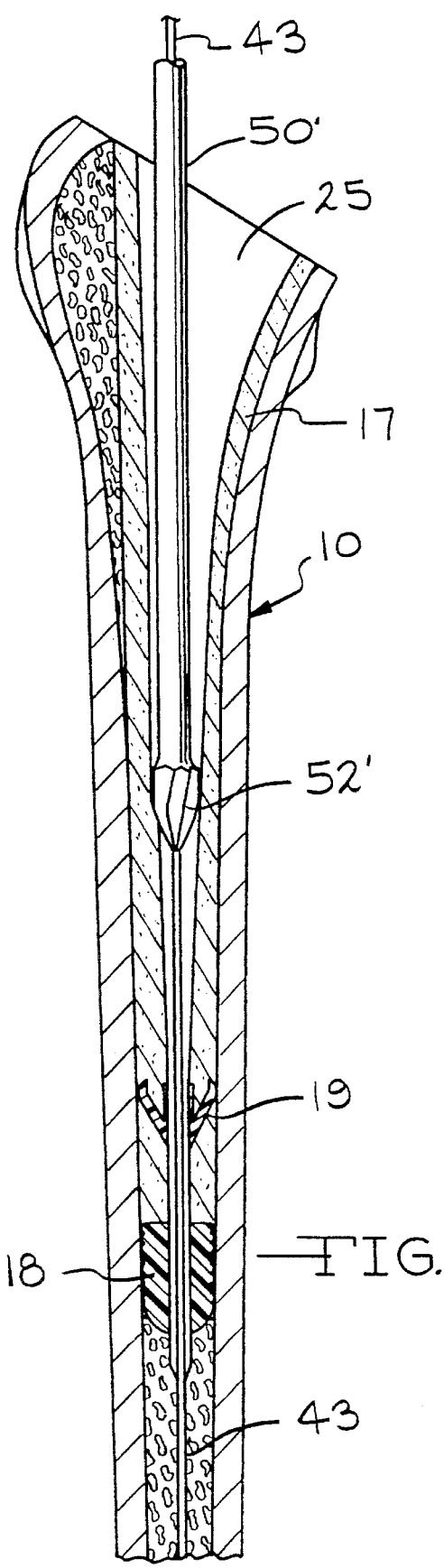
FIGS. 7 and 8 are views similar to FIG. 6 showing the femur as the canal is progressively enlarged with still larger reamers utilizing the bullit guidewire as a guide.
Figure 8:
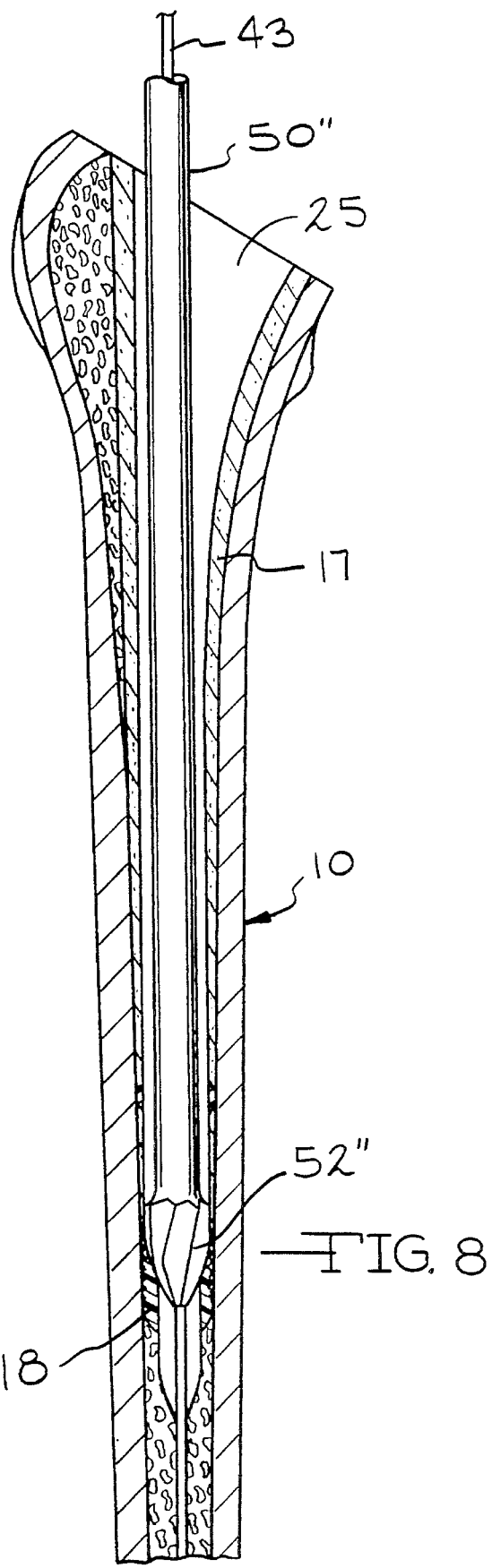

As can be seen in FIGS. 7 and 8, progressively larger reamers 50' (FIG. 7) and 50" (FIG. 8) with progressively larger cutting heads 52' and 52" are utilized to progressively enlarge the opening of the cavity 25 and remove the old cement 17, the centralizer 19 and the restricter 18 and to progressively enlarge the opening until all of the old cement 17 has been removed and in doing so to utilize the bullit guidewire 43 to guide it. If desired, as progressively larger reamers 50, 50' and 50" are used, larger diameter guidewires may be inserted, replacing the small guidewire 43 used for the drill bit 41. The larger guidewires will give additional rigidity in guiding the path of the reamers.

Figure 9:
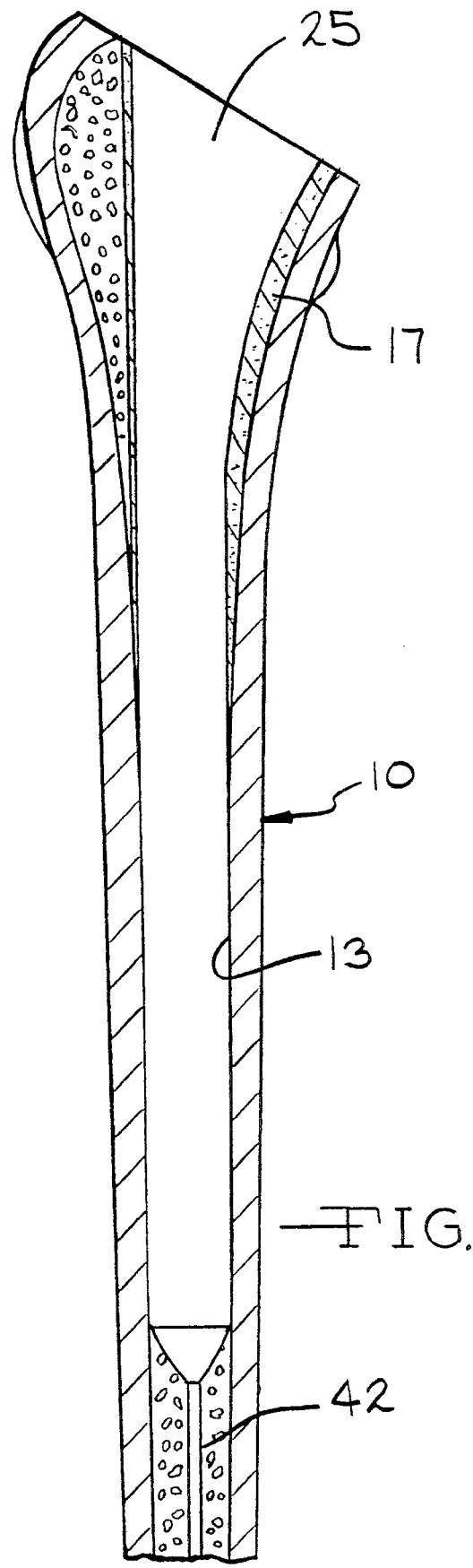
FIG. 9 is a sectional view of a femur prepared for revision surgery with the old cement removed and the guidewire removed.

Referring to FIG. 9, following reaming of the old cement 17 in the lower portion of the femur and reaming of the centralizer 19 and restricter 18, the reamer arid guidewire 43 may be removed. Although there will be additional old cement 17 still present in the upper, larger femur portion, it can be readily removed by conventional techniques.

Referring now to FIGS. 10–15, there is shown the method and apparatus for preparing a newly reamed cavity 57 of femur 56 preparatory to receiving a new femoral hip prosthesis for implantation. Although not limited to such use, the method and apparatus disclosed and claimed herein is ideally suited for preparing, in revision surgery, a femur to receive a collarless polished tapered femoral prosthesis of the type manufactured and sold by Zimmer, Inc., Warsaw, Ind. as shown in its brochure entitled "The CPT™ Hip System" (copy enclosed) which is incorporated herein by reference.

Following removal of the old prosthesis, old cement and old restricter, a new cement restricter or plug 60 is placed at or near the bottom of the cavity 57. Preferably, the restricter 60 is formed of plastic and has a central threaded cavity 61 formed therein. A guidewire 62 having external threads 63 on its free end is threadedly engaged to the restricter 60. A removable T-bar 64 of conventional design may be secured to the end of the guidewire 62 extending out of the cavity 57 of femur 56. One such T-bar is one manufactured and sold by Zimmer, Inc., under the name of T-Handle (Zimmer Shank) Item No. 6551-60 of the above-referenced brochure. The T-bar 64, when engaged to the guidewire 62 threadedly engaged to the restricter 60 may be used to position the restricter 60 in the cavity 57. While still attached to the guidewire 62, the T-bar 64 is impacted to drive the restricter 60 to its proper position in the cavity 57. The T-bar 64 is then removed from the guidewire 62 leaving the guidewire in place threadedly engaged to the restricter 60.

Referring now to FIG. 11, with the guidewire 62 and restricter 60 in place, crushed cancellous bone graft material 65 is then loosely packed in the cavity 57.

Figure 12:
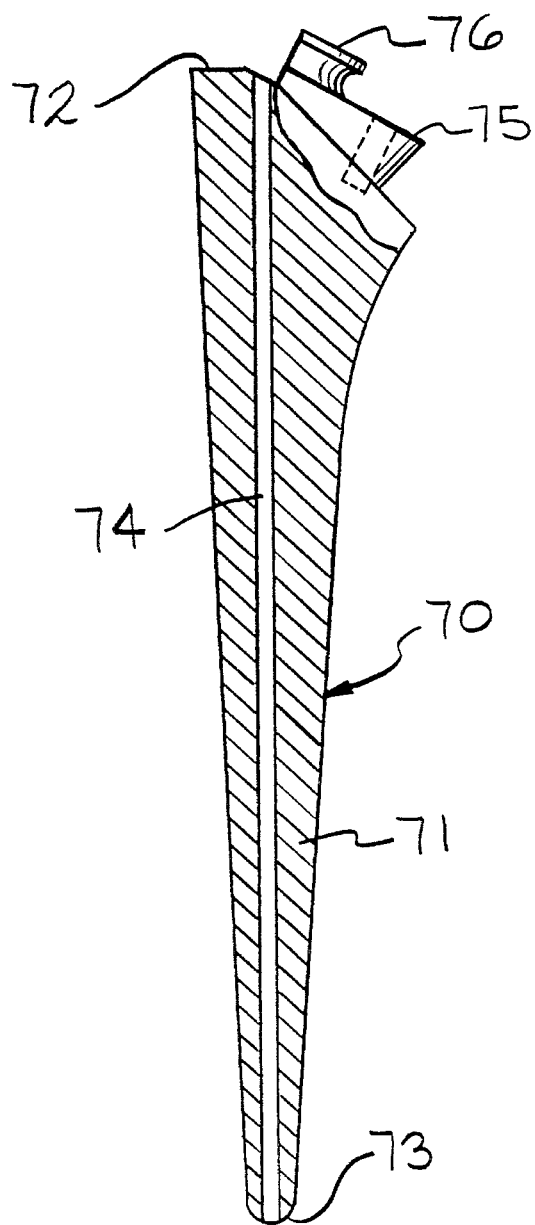
FIG. 12 is an elevational view of the cannulated tamp of the present invention.
Figure 14:
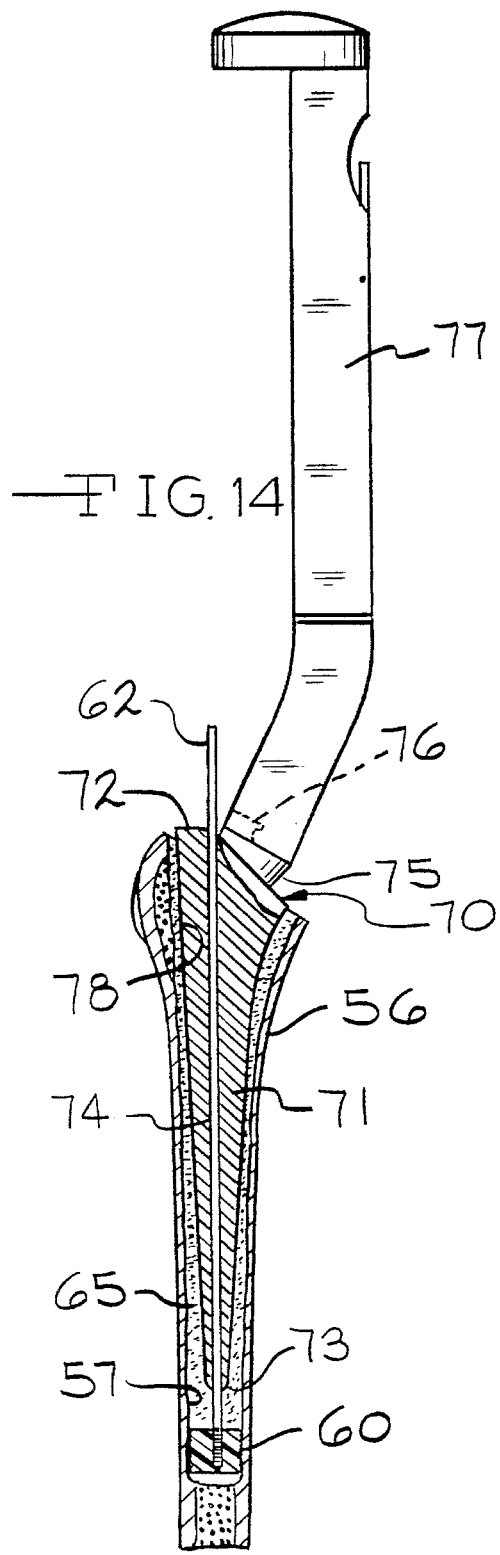
FIG. 14 is a sectional view showing the tamp with the guidewire extending therethrough positioned to compact bone graft material in the femur.

Referring now to FIGS. 12 and 14, there is shown a cannulated tamp generally designated by the numeral 70 which, in FIG. 14, is shown positioned in the cavity 57 of the femur 56 being prepared to receive a new femoral prosthesis. The tamp includes a stem portion 71 extending from an upper proximal end 72 to a lower distal end 73. The tamp 70 should have its stem 71 shaped similar to the shape of the femoral prosthesis intended to be implanted; however, ideally a series of tamps each of varying size will be utilized in performing a single revision surgery. Smaller sized tamps will be used initially with progressively larger ones used thereafter until the crushed cancellous bone graft material is compacted to the desired density and the new cavity thus formed will be of the desired size. The largest size tamp will be larger than the prosthesis intended to be implanted by an amount which will permit new bone cement used to implant such prosthesis to have a thickness of two to four millimeters in all portions of the stem. Thus, if the surgeon intends to use an implant of the type shown in the above-referenced Zimmer, Inc. brochure as a "CPT Hip Stem" the tamp 70 will have a stem configuration similar to that of the CPT Hip Stem. Preferably all portions of the stem 71 are polished to a smooth finish.

The tamp 70 has a longitudinal passageway 72. The upper or proximal end 72 of the tamp includes a protrusion 75 and knob 76 intended to be engaged by a rasp handle 77 of any desired type such as that disclosed in the above-referenced Zimmer, Inc. brochure as item No. 6601-05. It should be understood that since the longitudinal passageway 74 extends through the distal end 73 of the tamp 70, the tamp 70 may be slightly shorter than the prosthesis to be used in the revision. The passageway 74 must be large enough to permit the tamp 70 to move freely over the guidewire 62.

Figure 13:
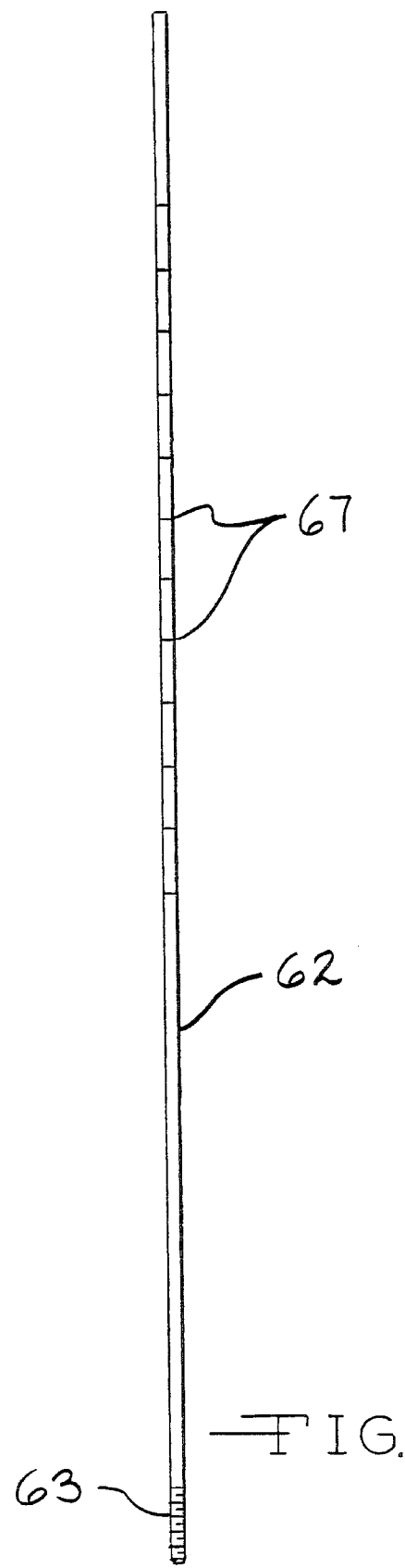
FIG. 13 is a view showing the guidewire to be used with the cannulated tamp in performing the method of the present invention.

Referring to FIG. 13, there is shown a detailed view of the guidewire 62. The guidewire 62 is approximately 2–5 mm in size, and in addition to the threads 63, may have a series of lines 67 for measuring depth to which the restricter is positioned.

Referring to FIG. 14, with the rasp handle 77 engaged to the tamp 70 by means of the protrusion 75 and knob 76, the tamp 70 is positioned to be driven into the cavity 57 by means of the rasp handle 76 being impacted by a hammer or other impacting device. With the tamp 70 positioned as indicated in FIG. 14 and with the guidewire 62 extending through the longitudinal passageway 74, the position of the tamp 70 is precisely controlled as it is driven to the desired position within the cavity 57. As will be appreciated by those skilled in the art, from time to time it may be necessary to completely remove the tamp 70 to place additional bone graft material 65 therein in order to provide the sufficient quantity of material for impacting to the proper density. Additionally, as previously noted, it may be desirable to utilize a series of tamps 70 beginning with a smaller tamp and working up progressively to one which is larger than the desired prosthesis to permit an adequate amount of bone cement around such prosthesis on implantation.

Following tamping of the cancellous bone graft material 65 to the desired density and the resultant formation of a cavity of the proper size and shape the tamp may be removed from the newly formed cavity 78, the rasp handle 77 removed therefrom, and the guidewire 62 may be unscrewed and removed from the restricter 60. The new cavity 78 is now ready to receive the new prosthesis.

Figure 15:
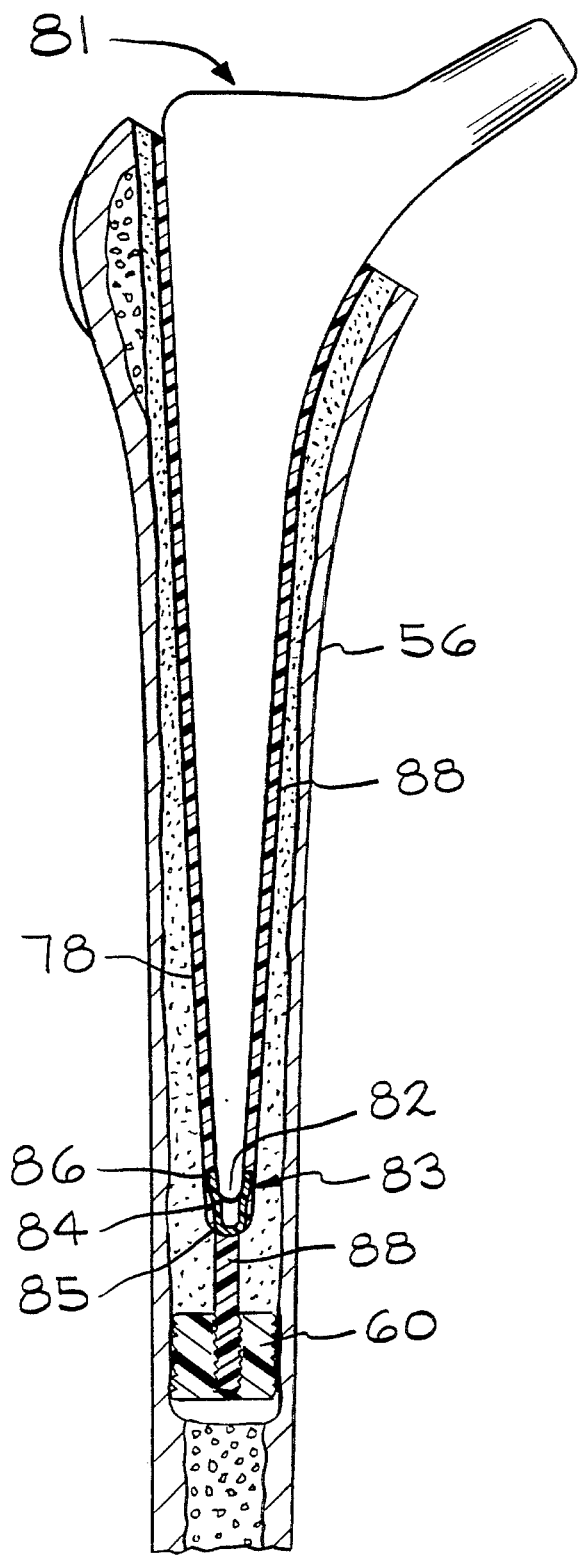
FIG. 15 is a sectional view showing a new prosthesis implanted in the femur.

FIG. 15 shows the completed revision surgery with a new prosthesis 81 having a distal end 82 positioned in a support element 83 implanted in bone cement 88. The support element 83 is formed of material suitable for implantation in a human body (such as PMMA) and has an annular sidewall 84 with a closed end 85 and an open top 86 in which the distal end 82 of the new prosthesis 81 is positioned. The distal end 82 is spaced from the closed end 85 to allow space for movement of such distal end 82 therein as the prosthesis 81, over time, subsides within the cement mantle 88 in which the new prosthesis is implanted. As will be appreciated and as can be seen in FIG. 15, the cement mantle 88 fills the cavity left by removal of the guidewire 62 from the restricter 60 and compacted bone graft.

The present invention may be used in revision surgery irrespective of whether the prosthesis to be replaced was implanted with bone cement or was one designed and used without cement. The new prosthesis should be implanted in cement following completion of bone graft as described above.

It is to be understood that the above detailed description of a preferred embodiment of the invention is provided by way of example only. Various details of design and construction and steps in the procedure may be modified without departing from the true spirit and scope of the invention as set forth in the appended claims.

We claim:

1. Apparatus for use in preparing a femoral cavity to receive (1) bone graft material and (2) a femoral hip prosthesis of predetermined size and configuration comprising in combination:
   (a) an elongate handle which is made of a material of suitable strength to transmit impacts made thereto;
   (b) a guidewire;
   (c) means for supporting said guidewire longitudinally in said cavity;
   (d) a cannulated tamp having a stem extending from a proximal end having a relatively large cross-sectional size and tapering to a distal end having a relatively small cross-sectional size, said stem having (1) a size larger than and a configuration similar to said femoral hip prosthesis and (2) a passageway sized to slideably receive said guidewire, said passageway extending from said proximal end to said distal end; and
   (e) means offset from said passageway extending from said proximal end for engagement by said handle, said proximal end and means for engagement being positioned to transmit impacts directed to said handle to said distal end, said tamp is made of a material having suitable strength to transmit impacts which compact crushed cancellous bone graft material to a desired density.

2. Apparatus according to claim 1, wherein said stem is polished to a smooth finish.

3. Apparatus according to claim 1, wherein said cannulated tamp is sized in relation to said femoral hip prosthesis to provide 2–4 millimeters of bone cement in all portions of said stem.

\* \* \* \* \*